| United States Patent [19] | [11] Patent Number: 5,396,004 |
| Arhancet et al. | [45] Date of Patent: Mar. 7, 1995 |

[54] COMPOSITIONS AND METHODS FOR INHIBITING VINYL AROMATIC MONOMER POLYMERIZATION

[75] Inventors: Graciela B. Arhancet, Katy; Inge K. Henrici, Spring, both of Tex.

[73] Assignee: Betz Laboratories, Inc., Trevose, Pa.

[21] Appl. No.: 118,075

[22] Filed: Sep. 8, 1993

Related U.S. Application Data

[63] Continuation-in-part of Ser. No. 964,321, Oct. 21, 1992, abandoned.

[51] Int. Cl.⁶ .............................................. C07C 7/20
[52] U.S. Cl. ........................................ 585/5; 585/3; 585/4; 208/48 AA; 252/402; 252/405
[58] Field of Search ............... 585/5, 4; 252/402, 405, 252/421; 208/48 AA

[56] References Cited

U.S. PATENT DOCUMENTS

| 4,720,566 | 1/1988 | Martin | 585/5 |
| 4,774,374 | 9/1988 | Abruscaro et al. | 585/24 |
| 4,915,873 | 4/1990 | Abruscaro et al. | 252/402 |
| 4,929,778 | 5/1990 | Roling | 585/3 |
| 4,956,020 | 9/1990 | Nakajima | 585/5 |

*Primary Examiner*—Asok Pal
*Attorney, Agent, or Firm*—Alexander D. Ricci; Philip H. Von Neida

[57] ABSTRACT

Methods and compositions are provided for inhibiting the polymerization of vinyl aromatic monomers under distillation conditions. The compositions comprise a combination of a phenylenediamine compound and a hydroxylamine compound.

6 Claims, No Drawings

COMPOSITIONS AND METHODS FOR INHIBITING VINYL AROMATIC MONOMER POLYMERIZATION

This is a continuation-in-part of application Ser. No. 07/964,321, filed Oct. 21, 1992, now abandoned.

FIELD OF THE INVENTION

The present invention relates to compositions and methods for inhibiting the undesirable polymerization of vinyl aromatics.

BACKGROUND OF THE INVENTION

Polystyrene is a thermoplastic with many desirable characteristics. It is clear, transparent, readily colored and easily fabricated. The family of styrene polymers includes polystyrene itself, copolymers of styrene with other vinyl monomers, polymers of derivatives of styrene and mixtures of polystyrene and styrene-containing copolymers with elastomers. Pure polystyrene is glass-like, transparent, hard, and rather brittle.

ABS (acrylonitrile, butadiene, styrene) and SAN (styrene, acrylonitrile) resins have enjoyed tremendous commercial popularity for many years as durable, temperature and solvent resistant elastomers. On the other hand, styrene plastics are commonly used for packaging, including foams and films, coatings, in appliance fabrication, for housewares and toys, lighting fixtures and in construction materials.

Common industrial methods for producing vinyl aromatic monomers, such as styrene, include a variety of purification processes, the most common one being distillation. It is well known that vinyl aromatic monomers readily polymerize when heated and that the rate of polymerization increases rapidly as the temperature increases. Thermal polymerization during distillation results not only in loss of product, but it could render the finished monomer unsuitable for using without further treatment.

To prevent polymerization of vinyl aromatic monomers under distillation conditions various inhibitor compositions have been employed. Unfortunately, although several compounds are effective against vinyl aromatic monomer polymerization under storage conditions, only some of these compounds have proved to be effective against polymerization under distillation conditions.

SUMMARY OF THE INVENTION

The present invention relates to compositions and methods for inhibiting polymerization of vinyl aromatic monomers during processes such as distillation of the vinyl aromatic monomer.

The composition comprises a mixture of a phenylenediamine compound and a hydroxylamine compound in a suitable solvent. This synergistic combination provides an effective method for inhibiting vinyl aromatic polymerization and does not require air to function.

DESCRIPTION OF THE RELATED ART

The compounds generally used commercially to prevent polymerization of vinyl aromatic monomers are of the dinitrophenolic type. For example, U.S. Pat. No. 4,105,506, Watson et al., teaches the use of 2,6-dinitro-p-cresol as polymerization inhibitor of vinyl aromatic compounds. U.S. Pat. No. 4,466,905, Butler et al., teaches that 2,6-dinitro-p-cresol and p-phenylenediamines will inhibit polymerization in the distillation column if oxygen is present. U.S. Pat. No. 4,774,374 Abruscato et al., teaches compositions and processes for inhibiting the polymerization of a vinyl aromatic compound employing an oxygenated species formed by the reaction of oxygen and a N-aryl-N'-alkyl-p-phenylenediamine. U.S. Pat. No. 4,720,566 Martin, teaches methods and compositions for inhibiting polymerization of acrylonitrile in the quench tower, no oxygen excluded, using a hydroxylamine compound and a phenyl p-phenylenediamine compound.

While these inventions may inhibit vinyl aromatic monomer polymerization, it would be advantageous to possess polymerization inhibitors that avoid the use of highly toxic compounds such dinitrophenols. It would also be advantageous that the inhibitor does not require air, or oxygen, to function.

DETAILED DESCRIPTION OF THE INVENTION

The present invention relates to compositions and methods for inhibiting the polymerization of vinyl aromatic monomer comprising a combination of a phenylenediamine compound and a hydroxylamine compound.

The hydroxyl amines useful in this invention have the formula

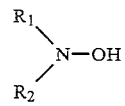

wherein $R_1$ and $R_2$ are the same or different and are hydrogen, hydroxyalkyl, alkoxyalkyl, alkyl, aryl, alkaryl or aralkyl groups.

Examples of suitable hydroxylamines include: hydroxylamine, N-methylhydroxylamine, N,N-dimethylhydroxylamine, N-ethylhydroxylamine, N,N-diethylhydroxylamine, N-(2-hydroxybutyl)hydroxylamine, N-(2-hydroxyethyl )hydroxylamine, N-(2-hydroxypropyl)hydroxyl amine, N,N-di-n-propylhydroxyl amine, N,N-di-n-butylhydroxylamine, N,N-diphenylhydroxylamine, N-benzylhydroxylamine, N,N-bis(ethylbenzyl)hydroxylamine, N,N-bis-(m-ethylbenzyl)hydroxylamine, N,N-bis-(p-ethylbenzyl)hydroxylamine, or mixtures thereof. Preferably, the hydroxylamine is N,N-bis(hydroxypropyl)hydroxylamine, also called hydroxypropylhydroxylamine (HPHA).

The phenylenediamine component of the inhibitor mixtures of this invention include phenylenediamine and derivatives thereof having at least one N—H group. It is thought that o-phenylenediamine or derivatives thereof having at least one N—H group are suitable in accordance with the instant invention. However, the preferred phenylenediamine is p-phenylenediamine having the formula

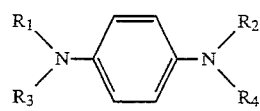

wherein $R_1$, $R_2$, $R_3$, and $R_4$ are the same or different and are hydrogen, alkyl, aryl, alkaryl, aralkyl groups with the proviso that at least one of $R_1$, $R_2$, $R_3$, or $R_4$ is hydrogen, more preferably the alkyl, aryl, alkaryl, and aralkyl groups have one to about twenty carbon atoms. The alkyl, aryl, alkaryl, and aralkyl groups may be straight or branched-chain groups. Exemplary p-phenylenediamines include p-phenylenediamine wherein R1, R2, R3, and R4 are hydrogen;

N-phenyl-N'-alkyl-p-phenylenediamines such as,
N-phenyl-N'-methyl-p-phenylenediamine,
N-phenyl-N'-ethyl-p-phenylenediamine,
N-phenyl-N'-propyl-p-phenylenediamine,
N-phenyl-N'-isopropyl-p-phenyldiamine,
N-phenyl-N'-n-butyl-p-phenylenediamine,
N-phenyl-N'-isobutyl-p-phenylenediamine,
N-phenyl-N'-sec-butyl-p-phenylenediamine,
N-phenyl-N'-tert-butyl-p-phenylenediamine,
N-phenyl-N'-n-pentyl-p-phenylenediamine,
N-phenyl-N'-n-hexyl-p-phenylenediamine,
N-phenyl-N'-(1-methylhexyl)-p-phenylenediamine,
N-phenyl-N'-(1,3-dimethylbutyl)-p-phenylenediamine,
N-phenyl-N'-(1,4-dimethylpentyl)-p-phenylenediamine;

N-phenyl-N',N'-dialkyl-p-phenylenediamines, such as
N-phenyl-N',N'-dimethyl-p-phenylenediamine,
N-phenyl-N',N'-diethyl-p-phenylenediamine,
N-phenyl-N',N'-di-n-butyl-p-phenylenediamine,
N-phenyl-N',N'-di-sec-butyl-p-phenylenediamine,
N-phenyl-N'-methyl-N'-ethyl-p-phenylenediamine;

N,N-dialkyl-p-phenylenediamines such as
N,N-dimethyl-p-phenylenediamine and
N,N'-diethyl-p-phenylenediamine;

N,N'-dialkyl-p-phenylenediamines such as
N,N'-di-isopropyl-p-phenylenediamine;

N,N'-diaryl-p-phenylenediamines such as
N,N'-diphenyl-p-phenylenediamine;

N,N,N'-trialkyl-p-phenylenediamines such as
N,N,N'-trimethyl-p-phenylenediamine,
N,N,N'-triethyl-p-phenylenediamine.

Preferably, the p-phenylenediamine is selected from the group consisting of N,N-dialkyl-p-phenylenediamine.

The compositions of the instant invention prove surprisingly effective in vinyl aomatic monomer that are substantially oxygen-free. By relatively oxygen-free, it is meant that little to no oxygen is dissolved in the vinyl aromatic monomer.

The total amount of phenylenediamine compound and hydroxylamine compound used in the methods of the present invention is that amount which is sufficient to effect inhibition of polymerization and will, of course, vary according to the conditions under which the vinyl aromatic monomer is being exposed to hot temperatures. At higher processing temperatures, large amounts of the polymerization inhibiting treatment are generally required.

Preferably, the total amount of the combined treatment (phenylenediamine compound and hydroxylamine compound) is from about 1 part per million to about 10,000 parts per million parts combined treatment based on the weight of the vinyl aromatic monomer. Most preferably, the total amount of the combined treatment is from about 5 parts per million to about 500 parts per million based on the weight of the vinyl aromatic monomer.

The phenylenediamine compound and hydroxylamine compound can be added to the vinyl aromatic monomer by any conventional method. The components can be added separately or as a combination containing both components. It is preferred to add the composition as a single treatment composition comprising both of the active vinyl aromatic monomer polymerization inhibitors.

Accordingly, it is therefore possible to produce a more effective vinyl aromatic polymerization inhibition treatment than is obtainable by use of either individual ingredient alone when measured at comparable treatment levels. Because of the enhanced polymerization activity of the combination, the concentration of each of the ingredients may be lowered and the total quantity of the polymerization inhibitor required for an effective treatment at elevated temperatures may be reduced.

The composition may be added to the vinyl aromatic monomer as either a dispersion or a solution using a suitable liquid carrier dispersing medium which is compatible with the vinyl aromatic.

The preferred inventive embodiment employs N,N'-di-sec-butyl p-phenylenediamine (PDA) and bis-N,N'(hydroxypropyl) hydroxylamine (HPHA). Optimal dosage rates are about 5 parts per million to about 500 parts per million of the combination per one million parts of the styrene monomer for which polymerization inhibition is desired.

EXAMPLES

The invention will now be further described with reference to a number of specific examples which are to be regarded solely as illustrative, and not as restricting the scope of the invention.

Freshly distilled styrene (70 ml) with an appropriate amount of inhibitor was placed in a 100 ml flask. The solution was purged with argon for 30 minutes and the liquid was heated to 100° C. or 120° C. in an oil bath. Argon spurging continued throughout the test. Samples were removed from the flask every half hour or 15 minutes and poured into 50 ml of methanol. The resulting polymer was filtered, dried overnight and then weighed. Results of this testing are reported in Tables I and II.

TABLE I

| | Styrene Reflux under Argon* at 100° C. Milligrams of Polymer vs. Time | |
|---|---|---|
| Time (min) | DNPC # 50 ppm mg polymer/5 mL | PDA/HPHA 25/25 ppm mg polymer/5 mL |
| 30 | 1 | 0 |
| 60 | 2 | 0 |
| 90 | 3 | 0 |
| 120 | 6 | 0 |

*less than 0.5 ppm of $O_2$
2,6-Dinitro-p-cresol

TABLE II

| | Styrene Reflux under Argon at 120° C. | |
|---|---|---|
| Time (min) | DNOC # 100 ppm mg polymer/5 mL | PDA/HPHA 25/25 ppm mg polymer/5 mL |
| 15 | 1 | — |
| 30 | 2 | 0 |
| 45 | 5 | 0 |
| 60 | 10 | 1 |

2,6-Dinitro-o-cresol

The same experiment as described above was carried out in the presence of air instead of argon. A styrene sample containing 100 ppm of PDA/HPHA was heated for six hours with no signs of polymerization. This data indicate that, in the presence of air, an even greater synergism exists between the two components.

As seen in Tables I–II, this combination proved more effective than known styrene polymerization inhibitors.

In another test, freshly distilled styrene (5 ml) with the appropriate amount of treatment was placed in a test tube. The test tube was capped with a septum and the solution was purged for 3 minutes with argon using two needles. The test tube was then placed for 2 hours in an oil bath heated at 100° C. At the end of this time, the styrene solution was cooled to room temperature and poured into 50 ml of methanol. The resulting polymer was filtered, dried, and reweighed. These results are shown in Table III.

TABLE III

| Treatment | Dose (ppm) | Polymer mg/5 mL |
| --- | --- | --- |
| Blank | — | 174 |
| PDA | 100 | 33 |
| PDA | 50 | 114 |
| PDA | 25 | 130 |
| HPHA | 100 | 70 |
| HPHA | 50 | 105 |
| HPHA | 25 | 141 |
| PDA/HPHA | 50/50 | 22 |
| PDA/HPHA | 25/25 | 60 |

The data in Table III clearly shows there is a synergistic effect between the two components of this invention.

While this invention has been described with respect to particular embodiments thereof, it is apparent that numerous other forms and modifications will be obvious to those skilled in the art. The appended claims generally should be construed to cover all such obvious forms and modification which are within the true spirit and scope of the present invention.

Having thus described the invention, what we claim is:

1. A method for inhibiting the polymerization of vinyl aromatic compounds undergoing distillation whereby said polymerization forms soluble polymers in said vinyl aromatic compounds comprising adding to said vinyl aromatic compounds a combination of a phenylenediamine compound and a hydroxyalkylhydroxylamine compound.

2. The method as claimed in claim 1 wherein said phenylenediamine compound is N,N'-di-sec-butyl p-phenylenediamine.

3. The method as claimed in claim 1 wherein said hydroxyalkylhydroxylamine compound is bis-N,N'(hydroxypropyl)hydroxylamine.

4. The method as claimed in claim 1 wherein the weight ratio of said phenylenediamine compound and said hydroxyalkyhydroxylamine compound ranges from 9:1 to about 1:9.

5. The method as claimed in claim 1 wherein the amount of said phenylenediamine compound and said hydroxyalkylhydroxylamine compound added, collectively, to said vinyl aromatic compounds is from about 1 part per million to about 10,000 parts per million parts of said vinyl aromatic compounds.

6. The method as claimed in claim 2 wherein said combination is added to said vinyl aromatic compound in a liquid carrier solvent.

* * * * *